United States Patent
Hsiao-Wecksler et al.

(10) Patent No.: US 9,662,263 B2
(45) Date of Patent: May 30, 2017

(54) FOREARM AND WRIST SUPPORT FOR CRUTCH USERS

(71) Applicant: The Board of Trustees of the University of Illinois, Urbana, IL (US)

(72) Inventors: Elizabeth T. Hsiao-Wecksler, Urbana, IL (US); Deen Farooq, Lombard, IL (US); Chenzhang Xiao, Champaign, IL (US); Girish Krishnan, Champaign, IL (US); Gaurav Singh, Urbana, IL (US); Ye Lwin Oo, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/882,292

(22) Filed: Oct. 13, 2015

(65) Prior Publication Data

US 2016/0101012 A1    Apr. 14, 2016

(51) Int. Cl.
*A61H 3/02* (2006.01)
*A61F 5/01* (2006.01)
*A61H 3/00* (2006.01)

(52) U.S. Cl.
CPC .............. *A61H 3/02* (2013.01); *A61F 5/01* (2013.01); *A61H 2003/006* (2013.01); *A61H 2003/007* (2013.01); *A61H 2201/1635* (2013.01)

(58) Field of Classification Search
CPC .......... A61H 3/02; A61H 3/00; A61H 3/0277; A61H 2201/1635; A61H 2201/0153; A61H 2003/006; A45B 2009/007; A45B 9/02; A45B 3/12; A61F 5/01; A61F 5/0118

USPC .............. 135/65, 66, 68, 71–73, 75, 82, 86; 602/20–22; 482/75
See application file for complete search history.

(56) References Cited

U.S. PATENT DOCUMENTS

| | | | |
|---|---|---|---|
| 3,113,897 A | | 12/1963 | Honningstad et al. |
| 5,564,451 A | * | 10/1996 | Hagberg ................. A61H 3/02 135/68 |
| 5,848,979 A | * | 12/1998 | Bonutti ................... A61F 5/013 482/45 |
| 5,938,240 A | * | 8/1999 | Gairdner ............ A63C 17/0013 135/85 |

(Continued)

FOREIGN PATENT DOCUMENTS

| | | | | |
|---|---|---|---|---|
| JP | WO 2005041844 A1 | * | 5/2005 | ............... A45B 9/00 |
| JP | 2009268655 A | * | 11/2009 | ............... A61H 3/00 |

OTHER PUBLICATIONS

"About Us." Creating Fluid Power Solutions at CCEFP. The Center for Compact and Efficient Fluid Power, 2013. Web. Sep. 25, 2013.

(Continued)

*Primary Examiner* — Winnie Yip
(74) *Attorney, Agent, or Firm* — Klintworth & Rozenblat IP LLC

(57) ABSTRACT

A crutch includes a pole, a cuff, a handle, a forearm support member, and a second forearm support member. The cuff and the handle are attached to the pole. The forearm support member, comprising an actuator, is disposed between the cuff and the handle and is moveable between a constricted position and a non-constricted position. The second forearm support member is disposed within the forearm support member. The energy generating device is configured to move the forearm support member between the constricted position and the non-constricted position.

50 Claims, 8 Drawing Sheets

(56) References Cited

U.S. PATENT DOCUMENTS

| | | | | |
|---|---|---|---|---|
| 5,951,499 | A | * | 9/1999 | Saringer ............ A61H 1/0274 601/33 |
| 6,085,765 | A | * | 7/2000 | Sigsworth ............ A61H 3/02 128/878 |
| 7,621,288 | B2 | * | 11/2009 | Evans ............ A61H 3/02 135/68 |
| 8,453,663 | B2 | * | 6/2013 | Zordan ............ A61H 3/02 135/65 |
| 8,474,470 | B2 | * | 7/2013 | Albertyn ............ A61H 3/02 135/69 |
| 8,564,144 | B1 | | 10/2013 | Rome et al. |
| 2009/0114257 | A1 | * | 5/2009 | Sutton ............ A61H 3/02 135/72 |
| 2011/0099765 | A1 | * | 5/2011 | Youssefieh ............ A01D 7/00 16/430 |
| 2011/0240077 | A1 | * | 10/2011 | Doherty ............ A61H 3/02 135/71 |
| 2013/0139861 | A1 | | 6/2013 | Spangler |
| 2013/0199586 | A1 | * | 8/2013 | Van Den Driesche .. A61H 3/02 135/69 |
| 2015/0040753 | A1 | * | 2/2015 | Bishop-Moser ......... F16J 1/006 92/254 |
| 2016/0151229 | A1 | * | 6/2016 | Varghese ............ A61H 3/02 135/71 |

OTHER PUBLICATIONS

Bishop-Moser, J., Krishnan, G., Kim, C., & Kota, S. Design of Soft Robotic Actuators using Fluid-filled Fiber Reinforced Elastomeric Enclosures in Parallel Combination, in proceedings of the IEEE International Conference for Intelligent Robot and Systems (IROS), Vilamoura, Algarve (Portugal), Oct. 7-12, 2012.

Bishop-Moser, J., Krishnan, G., & Kota, S. Force and moment generation of fiber-reinforced pneumatic soft actuators. In proceedings of the 2013 IEEE/RSJ International Conference on Intelligent Robots and Systems (IROS), 4460-4465, Nov. 2013.

Bishop-Moser, J., Krishnan, G., and Kota, S., Force and Hydraulic Displacement Amplification of Fiber Reinforced Soft Actuator, in proceedings of the 2013 ASME-IDETC Portland, Oregon, Aug. 5-8, 2013.

Center for Compact and Efficient Fluid Power. N.p.. Web. <http://www.ccefp.org>.

Dollar, A.M. and H. Herr, Lower Extremity Exoskeletons and Active Orthoses: Challenges and State-of-the-Art. IEEE Transactions on Robotics , 24(1): 144-158, 2008.

"Foot Splints." Foot Splints. N.p., n.d. Web. Sep. 21, 2012. <http://www.freemanmfg.com/product_info.php?products_id=424>.

Haubert, L.L., Gutierrez, D.D., Newsam, C.J., Gronley, J.K., Mulroy, S.J., Perry, J. A comparison of shoulder joint forces during ambulation with crutches versus a walker in persons with incomplete spinal cord injury. Archives of Physical Medicine & Rehabilitation 87, 63-70, 2006.

Herder J.L., Vrijlandt, N., Antonides, T. Cloosterman, M., Mastenbroek,PL. Principle and design of a mobile arm support for people with muscular weakness, JRRD, 43(5): 591-604, 2006.

Kaye, H.S., Kang, T., Laplante, M.P. Mobility Device Use in the United States. Disability Statistics Report, Washington, DC: US Department of Education, National Institute on Disability and Rehabilitation Research, pp. 1-60, 2000.

Klute, G., Czerniecki, J., and Hannaford, B. McKibben artificial muscles: pneumatic actuators with biomechanical intelligence, In Proceedings of 1999 IEEE/ASME International conference in Advanced Intelligent Mechatronics, pp. 221-226, 1999.

Konop KA, Strifling KM, Wang M, Cao K, Schwab JP, Eastwood D, Jackson S, Ackman JD, Harris GF. A biomechanical analysis of upper extremity kinetics in children with cerebral palsy using anterior and posterior walkers. Gait Posture, Oct; 30(3):364-9, 2009.

Krishnan, G., Bishop-Moser, J., Kim, C., & Kota. Evaluating the Mobility Behavior of Fluid Filled Fiber Reinforced Elastomeric Enclosures, proceedings of the 2012 ASME-IDETC/CIE, Chicago, IL, Aug. 15-17, 2012.

Lal, S. Premature degenerative shoulder changes in spinal cord injury patients. Spinal Cord 36 (3), 186-189, 1998.

Leung C.Y. and Yeh P.C. Vertical force and wrist deviation angle in a sample of elderly people using walkers, Perceptual and Motor Skills 116(1): 223-232, 2013.

Mercer, J.L., Boninger, M., Koontz, A., Ren, D., Dyson-Hudson, T., Cooper, R. Shoulder joint kinetics and pathology in manual wheelchair users. Clinical Biomechanics 21 (8), 781-789, 2006.

"Oandp.com." Beyond Control: The First Untethered Power-Assist AFO. N.p., n.d. Web. Sep. 21, 2012. <http://www.oandp.com/articles/2011-10_07.asp>.

"Orthotic." Merriam-Webster. Merriam-Webster, 2013. Web. Sep. 16, 2013.

Peel, L. D., Jensen, D. W., & Suzumori, K. Batch fabrication of fiber-reinforced elastomer prepreg. Journal of advanced materials, 30(3), 3-10, 1998.

Peel, L. D., Baur, J., Phillips, D., & McClung, A. The effect of scaling on the performance of elastomer composite actuators. In SPIE Smart Structures and Materials+ Nondestructive Evaluation and Health Monitoring (International Society for Optics and Photonics). 76441W-76441W, Mar. 2010.

Peel, L. D., Baur, J. W., & Justice, R. S.. Characterization and application of shape-changing panels with embedded rubber muscle actuators.Smart Materials and Structures, 22(9), 094020, 2013.

Shorter, Kenneth A., Jicheng Xia, Elizabeth T. Hsiao Wecksler, William K. Durfee, and Kogler F. Geza."Technologies or Powered Ankle-Foot Orthotic Systems: Possibilites and Challenges." IEEE/ASME Transactions of Mechatronics, 18 (1):377-347,2013.

Shorter, K.A., G.F. Kogler, E. Loth, W.K. Durfee, and E.T. Hsiao-Wecksler, A portable powered ankle-foot orthosis for rehabilitation. J Rehabil Res Dev, 48(4): 459-72, 2011.

Sie, I.H., Waters, R.L., Adkins, R.H., Gellman, H. Upper extremity pain in the postrehabilitation spinal cord injured patient. Archives of Physical Medicine and Rehabilitation 73 (1), 44-48, 1992.

Slavens, B.A., Sturm, P.F., Bajorunaite, R., Harris, G.F. Upper extremity dynamics during Lofstrand crutch-assisted gait in children with myelomeningocele. Gait and Posture 30, 511-517, 2009.

Slavens, B.A., Sturm, P.F., Harris, G.F. Upper extremity inverse dynamics model for crutch-assisted gait assessment. Journal of Biomechanics 43 (10), 2026-2031, 2010.

Slavens, B.A., Schnorenberg, A., Graf, A., Krzak, J., Smith, P. and Harris, G.F. Assisted Mobility Device Usage in Pediatric Orthopaedic Disabilities. Presented at the American Academy of Cerebral Palsy and Developmental Medicine (AACPDM) as part of Preconference Workshop 3: New Clinical Horizons and Emerging Mobility Technologies-A Research Driven Process. Oct. 16-19, 2013.

Waring 3rd, W.P., Werner, R.A. Clinical management of carpal tunnel syndrome in patients with long-term sequelae of poliomyelitis. J Hand Surg Am.14:865-9, 1989.

CCEFP podium presentation "Project 2F.1: Soft Pneumatic Actuator for Arm Orthosis," Annual Meeting/FPIRC 2014, October 15th, 2014.

Krishnan G, Rank R, Rokosz J, Carvey P, Kota S, 'A Strength Based Approach for the Synthesis of a Compliant Nonlinear Spring for an Orthotic Knee Brace', in proceedings of 2013 ASME—IDETC conference, Portland, OR, Aug. 5-8, 2013.

* cited by examiner

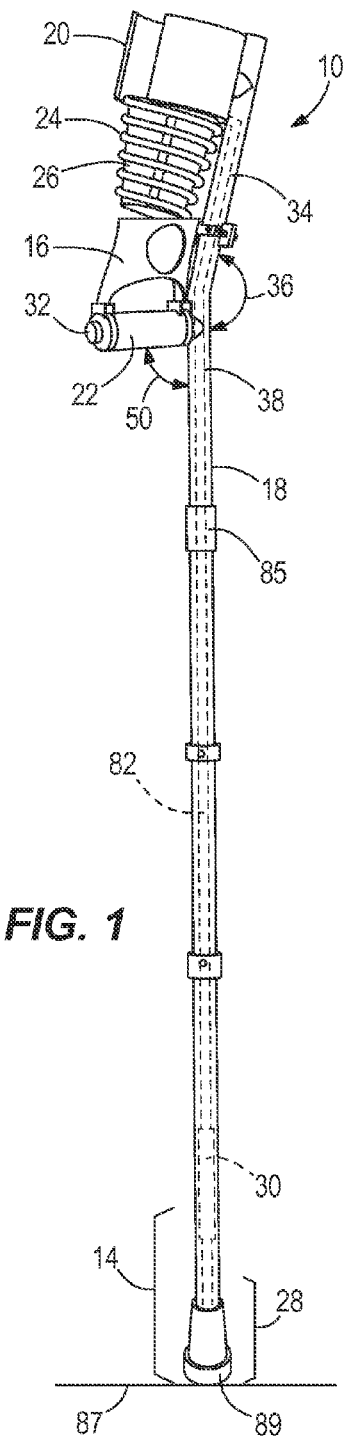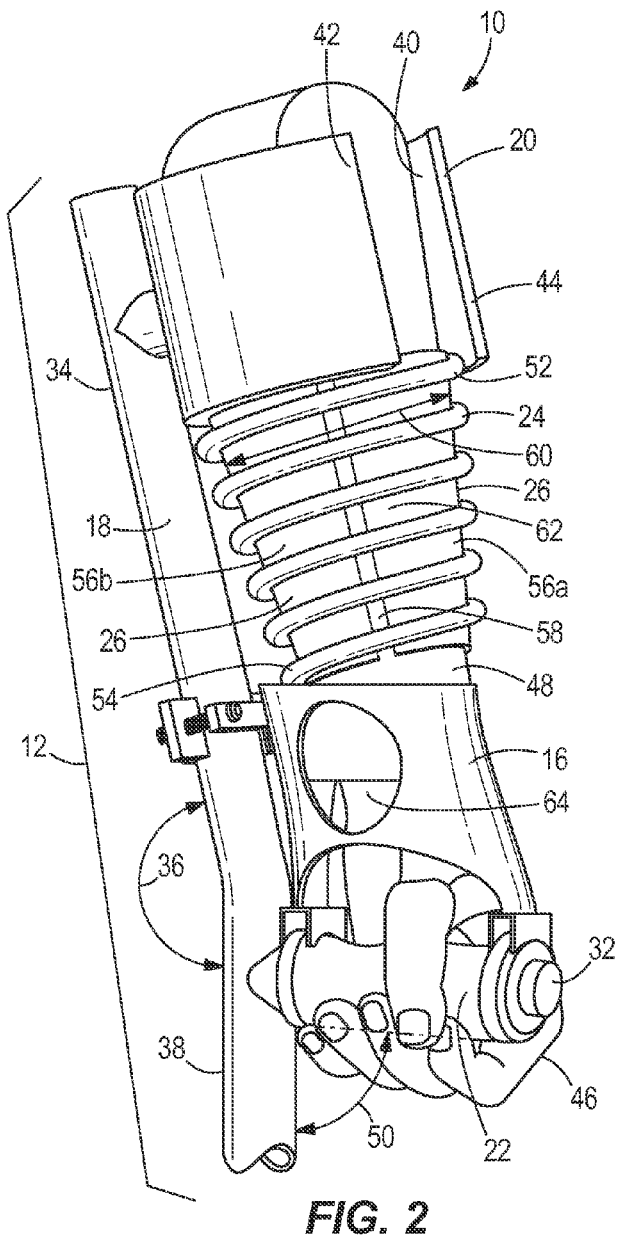
FIG. 1
FIG. 2

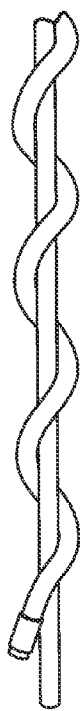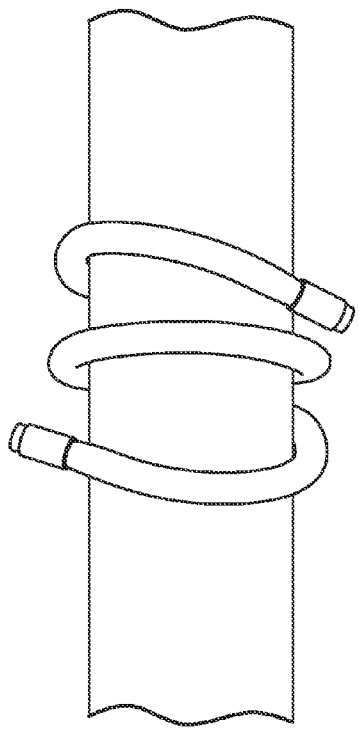
*FIG. 11A*    *FIG. 11B*    *FIG. 11C*    *FIG. 11D*

FOREARM AND WRIST SUPPORT FOR CRUTCH USERS

RELATED APPLICATIONS

The disclosure is a utility patent application claiming priority to and the benefit of U.S. provisional patent application Ser. No. 62/062,624, Pneumatics For Orthotics, filed on Oct. 10, 2014, which is hereby incorporated by reference in its entirety.

FIELD OF THE DISCLOSURE

This disclosure relates to crutches which provide additional support for crutch users.

BACKGROUND

Crutches typically put a large amount of stress on a user's wrists during use due to heavy load distribution on the user's wrists or due to too much bending movement of the wrists. This can create user injury or lead to other issues.

A crutch and method of use is needed to reduce or eliminate one or more issues of one or more of the current crutches.

SUMMARY

In one embodiment, a crutch includes a pole, a cuff, a handle, and a forearm support member. The cuff and the handle are attached to the pole. The forearm support member is disposed between the cuff and the handle and is moveable between a constricted position and a non-constricted position.

In another embodiment, a crutch includes a pole, a cuff, a handle, a forearm support member, and a second forearm support member. The cuff and the handle are attached to the pole. The forearm support member, comprising an actuator, is disposed between the cuff and the handle and is moveable between a constricted position and a non-constricted position. The second forearm support member is disposed within the forearm support member. The energy generating device is configured to move the forearm support member between the constricted position and the non-constricted position.

In still another embodiment, a method of using a crutch is disclosed. In one step, a user's hand is inserted through a cuff of a crutch while a forearm support member of the crutch, disposed between the cuff and a handle of the crutch, is disposed in a non-constricted position. In another step, the user's hand grips the handle of the crutch. In still another step, the forearm support member of the crutch is moved from the non-constricted position to a constricted position to provide support to the user's forearm.

The scope of the present disclosure is defined solely by the appended claims and is not affected by the statements within this summary.

BRIEF DESCRIPTION OF THE DRAWINGS

The disclosure can be better understood with reference to the following drawings and description. The components in the Figures are not necessarily to scale, emphasis instead being placed upon illustrating the principles of the disclosure.

FIG. 1 a front view of one embodiment of a crutch;

FIG. 2 illustrates a perspective view of a top portion 12 of the crutch 10 of the embodiment of FIG. 1;

FIGS. 11A-11D are photographic images of fabricated embodiments of the helical fiber-reinforced actuator.

DETAILED DESCRIPTION

Figure 3:
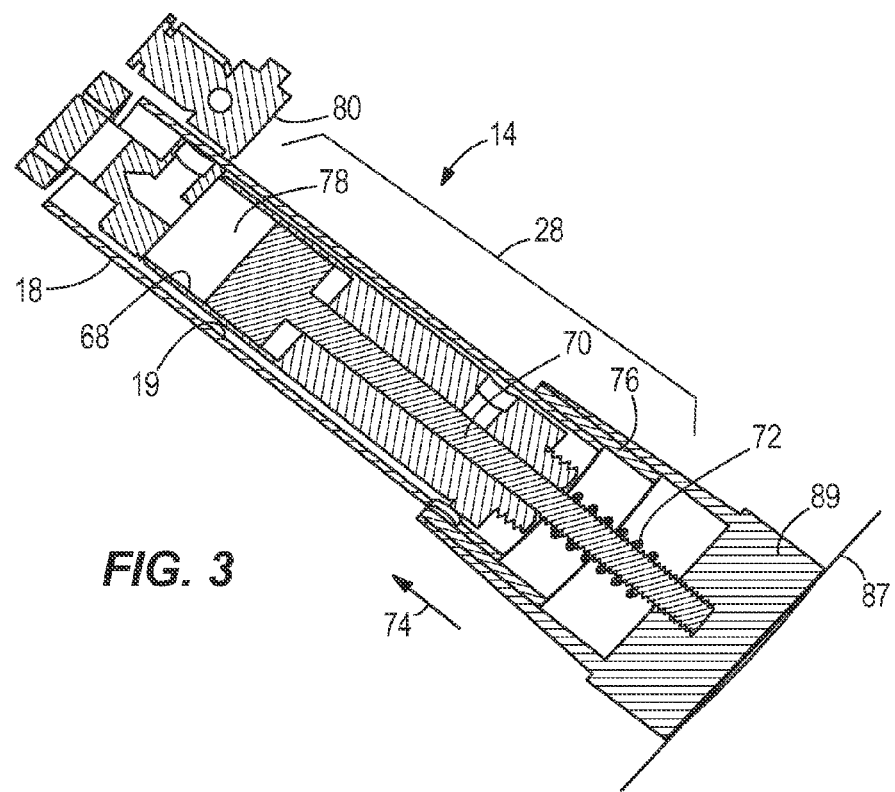
FIG. 3 illustrates a cross-sectional view of a bottom portion 14 of the crutch 10 of the embodiment of FIG. 1.
Figure 4:
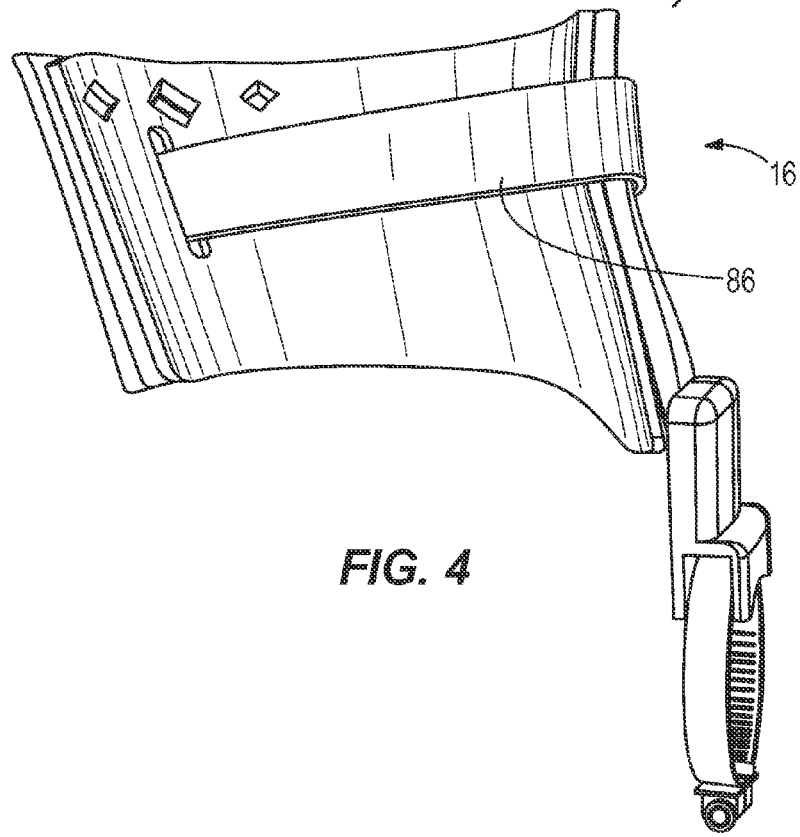
FIG. 4 illustrates a side view of a wrist support member 16 detached from the crutch 10 of the embodiment of FIG. 1.

FIG. 1 illustrates a front view of one embodiment of a crutch 10. FIG. 2 illustrates a perspective view of a top portion 12 of the crutch 10 of the embodiment of FIG. 1. FIG. 3 illustrates a cross-sectional view of a bottom portion 14 of the crutch 10 of the embodiment of FIG. 1. FIG. 4 illustrates a side view of a wrist support member 16 detached from the crutch 10 of the embodiment of FIG. 1.

As shown collectively in FIGS. 1-4, the crutch 10 comprises the wrist support member 16, a pole 18, a cuff 20, a handle 22, a forearm support member 24, a second forearm support member 26, an energy generating device 28, an energy storage device 30, and a control member 32. In other embodiments, the crutch 10 may comprise differing components in differing orientations and configurations.

The crutch 10 may comprise a Lofstrand crutch. In other embodiments, the crutch 10 may vary including auxiliary (under-arm crutches) and other types of crutches. The pole 18 comprises at least one hollow shaft 19. A first portion 34 of the pole 18 is disposed at a non-parallel angle 36 to a second portion 38 of the pole 18. In other embodiments, the pole 18 may comprise other shapes, parts, configurations, or orientations. The cuff 20 is attached to the first portion 34 of the pole 18 using fasteners or other attachment mechanisms. The cuff 20 comprises a gap 40 disposed between opposed ends 42 and 44 of the cuff 20. The cuff 20 is made of a flexible material such as plastic that allows the opposed ends 42 and 44 to move towards or away from one another. The cuff 20 is sized to allow a user's hand 46 and forearm 48 to be inserted through the cuff 20 so that the user's hand 46 may grip the handle 22. The flexibility of the cuff 20 allows the cuff 20 to accommodate varying sized user hands and user forearms.

The handle 22 is attached to the second portion 38 of the pole 18. The handle 22 is attached to the second portion 38 of the pole 18 using fasteners or other attachment mechanisms. The handle 22 is disposed at a right angle 50 relative to the second portion 38 of the pole 18. In other embodiments, the handle 22 may be disposed in varying orientations relative to the pole 18.

The forearm support member 24 is disposed between the cuff 20 and the handle 22. Opposed ends 52 and 54 of the forearm support member 24 are attached to the second forearm support member 26. In other embodiments, either of the opposed ends 52 and 54 or any portion of the forearm support member 24 may be directly attached to any part of the crutch 10 such as to the pole 18 or to the cuff 20. The forearm support member 24 may comprise an actuator, a fiber-reinforced actuator, or a fiber-reinforced elastomeric enclosure as disclosed in US Pat Pub #2015/0040753, entitled Fiber-Reinforced Actuator and published on Feb. 12, 2015, which is hereby incorporated by reference. In other embodiments, the forearm support member 24 may comprise a mechanically operated device, a strap, a belt, any type of electrically activated device, any type of hydraulic or pneumatic activated device, or further varying types of members or devices.

The second forearm support member 26 is disposed within the forearm support member 24. The second forearm support member 26 comprises shells 56a and 56b that may be flexibly attached to the cuff 20. The second forearm support member 26 may be attached to the cuff 20 using any type of attachment mechanism such as fasteners, adhesive, or other attachment mechanisms. A gap 58 is disposed in the second forearm support member 26 to allow the second forearm support member 26 to be compressed. In another embodiment, the second forearm support member 26 may comprise any number of members or shells in varying orientations, configurations, and locations relative to the forearm support member 24. In still another embodiment, the second forearm support member 26 may not be present at all.

The forearm support member 24 is moveable between a non-constricted position and a constricted position. In the non-constricted position, the dimension 60 of the inner shaft 62 of the forearm support member 24 is increased to allow a user to insert their hand 46 and forearm 48 into the second forearm support member 26. In the constricted position, the dimension 60 of the inner shaft 62 of the forearm support member 24 is decreased to distribute load from the user's forearm 48 into the second forearm support member 26, through the cuff 20, and into the pole 18 to reduce load on the user's wrist 64 as the user's hand 46 grips the handle 22. This reduces the likelihood of the user incurring injury due to too high of loads being placed on the user's wrist 64 as the user's hand 46 grips the handle 22.

The energy generating device 28 is attached to and within the inner shaft 19 at a bottom portion 14 of the pole 18. In other embodiments, the energy generating device 28 may be attached inside or outside the pole 18 at any location. The energy generating device 28 is adapted to move the forearm support member 26 between the constricted position and the non-constricted position. The energy generating device 28 comprises a pneumatic device generating pneumatic energy. In other embodiments, the energy generating device 28 may comprise a hydraulic device generating hydraulic energy, an electrical device generating electrical energy, a mechanical device generating mechanical energy, or another type of energy generating device generating varying types of energy. The energy generating device 28 comprises a chamber 68 containing a piston 70 biased by a spring 72 in direction 74. Ideally, the spring 72 comprises one or more conical springs which when compressed flatten into a disc to allow longer travel of the piston 70. A linear bearing 76 holds the piston 70 in place. A gas 78 is disposed in the chamber 68. One or more valves 80 connect the chamber 68 to one or more tubes 82. The one or more tubes 82 are connected between the valves 80, the energy storage device 30, one or more valves 85, the control member 32, and the forearm support member 24. The one or more tubes 82 extend within the inner shaft 19 of the pole 19. In other embodiments, the one or more tubes 82 may extend outside of the pole 19.

The energy storage device 30 is attached to and within the inner shaft 19 of the pole 18. In other embodiments, the energy storage device 30 may be attached to and outside of the pole 18. The energy storage device 30 stores energy (in this case the energy storage device 30 is an accumulator which stores the gas 78 since the system is pneumatic) generated by the energy generating device 28. In other embodiments, the energy storage device 30 stores whatever type of energy is generated by the energy generating device 28 (i.e. hydraulic energy, electrical energy, mechanical energy, etc.). For instance, in varying embodiments, the energy storage device 30 may comprise a gas storing device, a liquid storing device, an electrical storing device such as battery, a mechanical storage device, or another type of energy storage device.

When a user uses the crutch 10 to walk on a surface 87, the piston 70 of the energy generating device 28 is forced to move in direction 74 as the piston 70 contacts the surface 87 thereby compressing the spring 72. The piston 70 is connected to an end cap 89. The control member 32 allows the user to control the one or more valves 80 and 85 to control when the energy (in this case the gas 78) flows from the energy storage device 30, through the one or more valves 85, and into the forearm support member 24 in order to move the forearm support member 24 from the non-constricted position to the constricted position to distribute the load from the user's forearm 48 into the second forearm support member 26, through the cuff 20, and into the pole 18 to reduce load on the user's wrist 64 as the user's hand 46 grips the handle 22. This reduces the likelihood of the user incurring injury due to too high of loads being placed on the user's wrist 64 as the user's hand 46 grips the handle 22.

The control member 32 also allow the user to control the one or more valves 85 to control when the energy (in this case the gas 78) is let out of the forearm support member 24 in order to move the forearm support member 24 from the constricted position to the non-constricted position so that the user can retract or insert the user's forearm 48 and hand 46 from or into the second forearm support member 26. The control member 32 is attached to the handle 22. In other embodiments, the control member 32 may be attached to any portion of the crutch 10. The control member 32 may comprise a button, a toggle, a lever, a switch, or another type of control member. In other embodiments, the crutch 10 may utilize varying components in varying locations, positions, orientations, or configurations in order to move the forearm support member 24 between the non-constricted position and the constricted position.

The wrist support member 16 is attached to the pole 18 and to the handle 22 using fasteners or other attachment mechanisms. In other embodiments, the wrist support member 16 may be attached to either the pole 18 or to the handle 22, or to another component of the crutch 10. The wrist support member 16 supports the user's hand 46 in a neutral position so that the user's hand 46 and forearm 48 are substantially collinear while the user's hand 46 grips the handle 22. The use of the wrist support member 16 reduces the likelihood of the user experiencing carpal tunnel syndrome or other injury due to repetitive bending of the user's wrist 64. In one embodiment, the wrist support member 16 supports the user's hand 46 in a neutral position so that the user's hand 46 and forearm 48 are within 10 degrees of being collinear while the user's hand 46 grips the pole 18. In another embodiment, the wrist support member 16 supports the user's hand 46 in a neutral position so that the user's hand 46 and forearm 48 are within 5 degrees of being collinear while the user's hand 46 grips the pole 18. In one embodiment, the wrist support member 16 supports the user's hand 46 in a neutral position so that the user's hand 46 and forearm 48 are within 2.5 degrees of being collinear while the user's hand 46 grips the pole 18.

The wrist support member 16 is substantially parallel to the second portion 38 of the pole 18. In one embodiment, the wrist support member 16 is within 10 degrees of being parallel to the second portion 38 of the pole 18. In one embodiment, the wrist support member 16 is within 5 degrees of being parallel to the second portion 38 of the pole 18. In one embodiment, the wrist support member 16 is within 2.5 degrees of being parallel to the second portion 38 of the pole 18. The wrist support member 16 further comprises a support member 86 to support the user's wrist 64 in a neutral position. The support member 86 comprises a strap. The tension of the support member 86 may be adjusted to comfortably accommodate the user's wrist 64 into the neutral position. In other embodiments, the support member 86 may comprise any type of support member for supporting the user's wrist 64 in the neutral position. In other embodiments, the wrist support member 16 may have varying components or further vary in design, location, configuration, or orientation.

In still other embodiments, the crutch 10 and any of its components may vary in design, type, number, location, configuration, or orientation, and/or one or more additional components may be added to the crutch 10.

Figure 5:
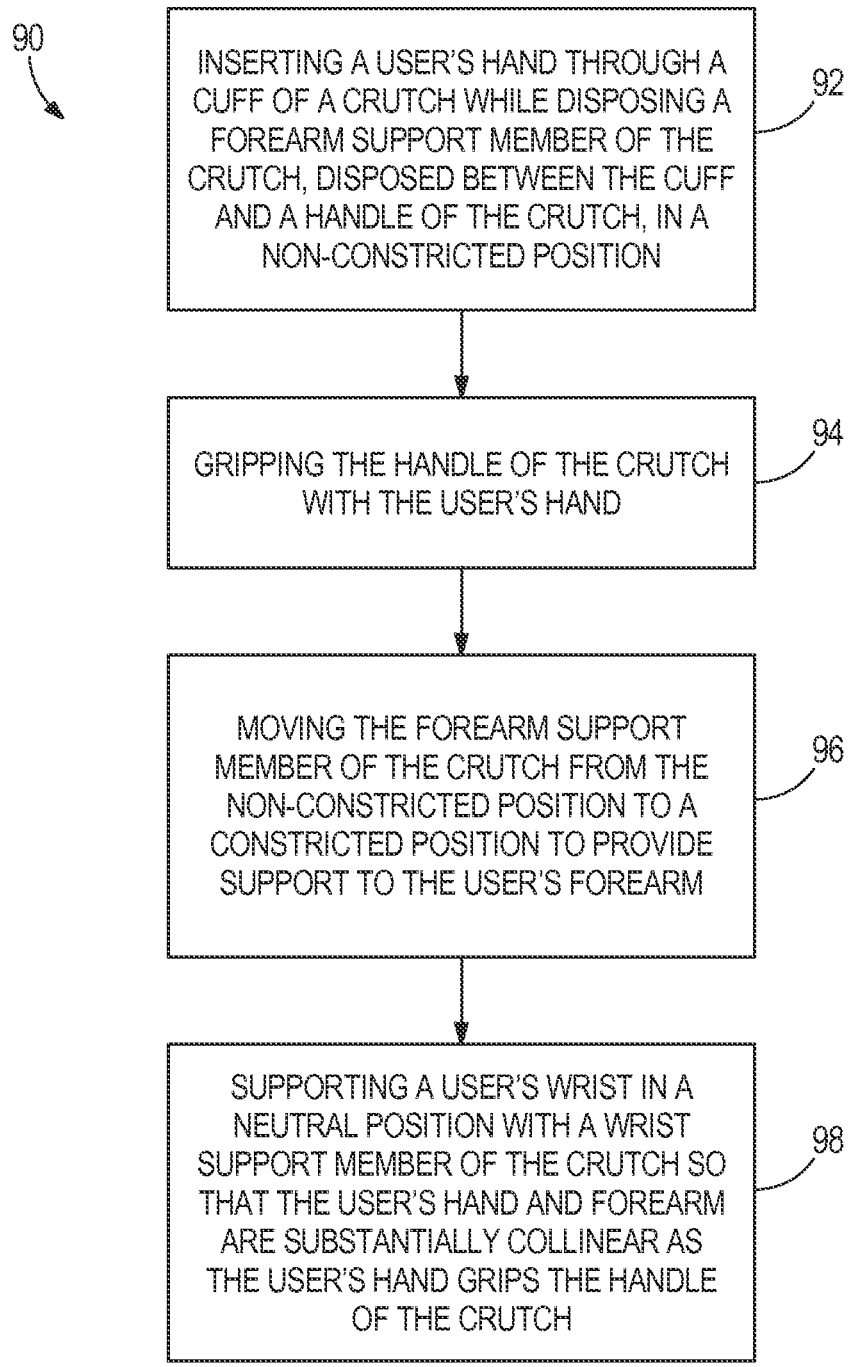
FIG. 5 illustrates a flowchart of one embodiment of a method 90 of using a crutch.

FIG. 5 illustrates a flowchart of one embodiment of a method 90 of using a crutch. The method 90 may utilize any of the crutch embodiments of the instant disclosure. In step 92, a user's hand is inserted through a cuff of a crutch while a forearm support member of the crutch, disposed between the cuff and a handle of the crutch, is disposed in a non-constricted position. In one embodiment, the crutch may comprise a Lofstrand crutch. In other embodiments, the crutch may vary to comprise any type of crutch. In one embodiment, the forearm support member may comprise an actuator. In another embodiment, the forearm support member may comprise a fiber-reinforced actuator. In still another embodiment, the forearm support member may comprise a fiber-reinforced elastomeric enclosure. In step 94, the handle of the crutch is gripped with the user's hand. In step 96, the forearm support member of the crutch is moved from the non-constricted position to a constricted position to provide support to the user's forearm.

In one embodiment, step 96 further comprises constricting a second forearm support member disposed within the forearm support member to provide support to the user's forearm. The second forearm support member may comprise at least one shell flexibly attached to the cuff. In other embodiments, the second forearm support member may vary. In one embodiment, step 96 further comprises an energy generating device moving a forearm support member comprising an actuator between the constricted position and the non-constricted position. The energy generating device may be pneumatic, hydraulic, electrical, mechanical, or another type of energy generating device. In one embodiment, step 96 further comprises an energy storage device providing stored energy, generated by an energy generating device, to a forearm support member comprising an actuator to move the actuator between the constricted position and the non-constricted position. In one embodiment, step 96 further comprises a control member controlling when the forearm support member is in the constricted position and when the forearm support member is in the non-constricted position.

In step 98, a user's wrist is supported in a neutral position with a wrist support member of the crutch so that the user's hand and forearm are substantially collinear as the user's hand grips the handle of the crutch. In one embodiment, the wrist support member is attached to the handle or a pole of the crutch. In one embodiment, the wrist member is substantially parallel to a portion of a pole of the crutch. In one embodiment, step 98 further comprises supporting the user's wrist in a neutral position with a support member of the crutch.

In other embodiments, one or more steps of the method 90 may be varied in substance or order, one or more steps of the method 90 may not be followed, or one or more additional steps may be added to the method. In still other embodiments, the method 90 may further vary.

Described below is a fiber-reinforced actuator capable of complex and predictable movement and/or freedom of movement which may be used for the forearm support member 24 of the instant disclosure. Sets of fibers are oriented at unconventional angles along a control volume and at least partially constrain movement of an actuator body with which they are coupled. The fiber-reinforced actuator can be configured to provide rotational motion, a combination of rotational and axial motion, a change in rigidity, axial force, torsional force, and/or a combination of axial and torsional forces in response to work performed on the control volume.

One particular example of the fiber-reinforced actuator is a fiber-reinforced elastomeric enclosure (FREE). This particular type of actuator includes fibers wrapped about and along an elastomeric body in a given configuration. The fibers are disposed over or are at least partially embedded in the elastomer such that fluid pressure and/or volume displacement predictably actuates the enclosure. FREEs potentially offer vastly superior performance over other types of actuators, such as robotic or mechanical devices, with lightweight construction, energy efficient operation, providing enhanced functionality, and greater simplicity. It should be understood that the various combinations of fiber configurations disclosed and described herein are not limited to use with elastomeric enclosures or for exclusive use with fluidic control volumes. Rather, the ability to configure fibers with respect to a control volume to controllably constrain an actuator body with a predictable response according to the following teachings is useful with a wide range of materials and shapes.

Figure 6:
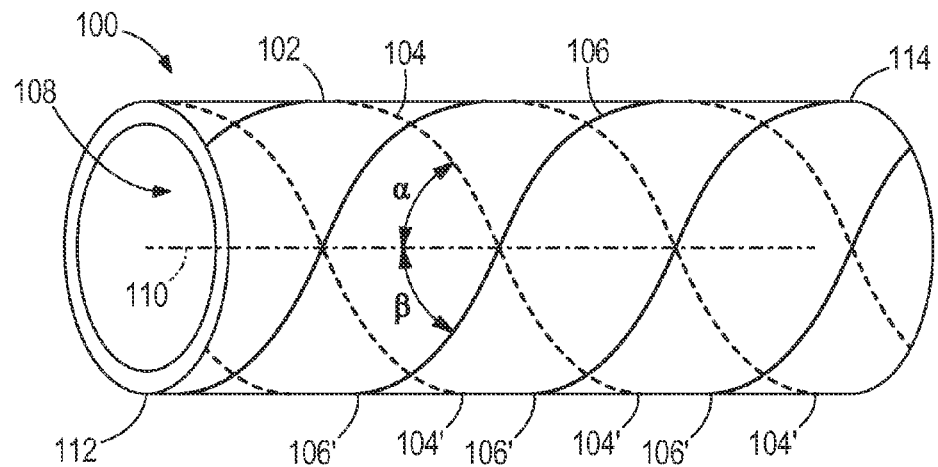
FIG. 6 is a schematic side view of an embodiment of a fiber-reinforced actuator.

FIG. 6 is a schematic side view of an example of a fiber-reinforced actuator 100, including a body 102, a first set of fibers 104, and a second set of fibers 106. The actuator body 102 has an associated control volume 108 with a central axis 110. In the illustrated example, the body 102 is tubular with a cylindrical control volume 108 and extends for some length along the control volume in the direction of the axis 110. One or both of opposite ends 112, 114 may be a closed end to partially define the control volume 108. In one embodiment, a first end 112 is configured for attachment to a fluid pressure source and the opposite second end 114 is a closed end, such that, when attached to the pressure source, the pressure of the control volume 108 is determined by the pressure of the fluid source.

The fibers of the first set 104 are oriented at an angle α relative to the central axis 110, and the fibers of the second set 106 are oriented at an angle β relative to the central axis. For purposes of notation in this disclosure, each fiber angle α, β is measured with the central axis 110 assigned a value of 0°, and each angle has a value and a sign (i.e., positive or negative). The value of each angle is between 0° and 90° inclusive, and the sign of each angle is determined by which direction the 0° to 90° angle is measured from the axis. The respective signs of the angles α and β are somewhat arbitrary, in that the direction of measurement depends on which side the actuator is viewed from. The significance of the sign of each angle α, β is whether they are the same or opposite signs. Generally, when the fibers of the first set 104 are slanted in the same direction as the fibers of the second set 106 when viewed from the side as shown, the angles α and β have the same sign. Likewise, when the fibers of the first set 104 are slanted in the opposite direction as the fibers of the second set 106, as is the case in the example of FIG. 6, the angles α and β have opposite signs. For purposes of this disclosure, fibers slanted like the first set 104 in FIG. 6 are considered to have a positive angle, and fibers slanted like the second set 106 in FIG. 6 are considered to have a negative angle.

Each set of fibers 104, 106 includes a plurality of individual fibers 104', 106'. In the illustrated example, each set 104, 106 includes three individual fibers, with the individual fibers arranged parallel with each other within each set in a helical manner about the circumference of the body 102. The number of individual fibers in any set of fibers may be any number of two or more.

In the particular example of FIG. 6, the angle α of the fibers of the first set 14 is equal in value and opposite from the angle β of the fibers of the second set, or α=−β. Depending on the value of the fiber angles, this type of actuator exhibits extension or contraction in the direction of the central axis 110 when the pressure of the control volume 108 is increased. In other words, the fibers constrain movement of the body in a manner that distributes the forces due to the pressure increase tend to cause the body to lengthen or shorten. While this type of movement, similar to the above-described pneumatic cylinder, is useful, other combinations of angle values and directions are available that result in rotational movement or torsional force, in some cases in combination with axial movement or force. Yet other combinations are useful to increase the stiffness of the actuator 100 while allowing freedom of movement in one or more translational or rotational directions.

Figure 7:
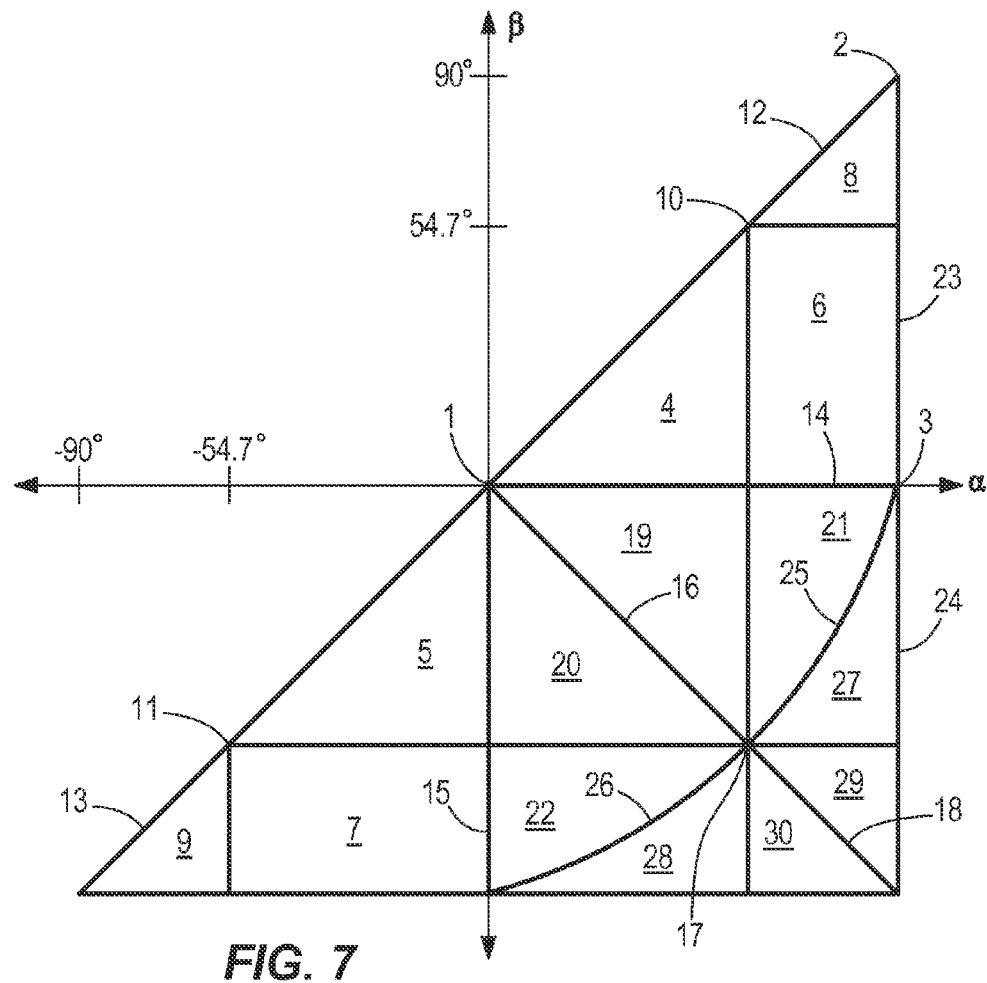
FIG. 7 is a chart illustrating various different regions of the available design space for the fiber-reinforced actuator with a fiber set at an angle $\alpha$ and a fiber set at an angle $\beta$.

FIG. 7 is a chart illustrating various regions 1-30 of a design space for the fiber-reinforced actuator. Each region is represented as a point, a segment, or an area in the chart of FIG. 7, and each adjacent region differs in at least one mobility direction. Types of mobility directions include an actuation direction and a freedom direction. The possible mobility directions are axial extension, axial contraction, counter-clockwise (CCW) rotation, clockwise (CW) rotation, transverse bending, combined CCW rotation and axial extension, combined CW rotation and axial extension, combined CCW rotation and axial contraction, combined CW rotation and axial contraction, combined CW rotation and transverse bending, and combined CCW rotation and transverse bending. Clockwise and counter-clockwise rotational directions are as viewed from the center of the actuator looking toward an end. For example, the actuator described by α=−β is represented in FIG. 7 by regions 16-18, including segments 16 and 18 and point 17. An actuator with fibers oriented in accordance with regions 16 and 18 respectively have axial contraction and axial expansion actuation directions when work is performed on the control volume. An actuator with fibers oriented as in region 17 has no actuation direction. None of regions 16-18 has a rotational actuation direction. Each of these regions also has multiple freedom directions, which are discussed in further detail below.

The actuator may be constructed to include a mobility direction with a rotational component. In one embodiment, the fiber-reinforced actuator is constructed such that α≠±β, and the orientation of the fibers of the first and second sets of fibers meets one of the following criteria:
−90°>α>90° and −90°>β>90°; or
α=90° and β≠0,
encompassing at least regions 4-9, 14-15, and 19-30 of FIG. 7. In another embodiment, fibers of the first set are non-parallel with fibers of the second set, and the sets of fibers are oriented such that, when work is performed on the control volume, the actuator exhibits a pre-determined motion response that includes a moment about the central axis. The moment may be a torsional force or may result in rotation about the central axis.

The chart of FIG. 7 includes certain threshold values and regions along with certain symmetrical characteristics. One set of threshold values is where either set of fibers is oriented at ±tan$^{-1}$[√2], approximated in FIG. 7 as ±54.7°, representing a boundary between several adjacent regions. The curved segments representing regions 25 and 26 are threshold regions, representing boundaries between other regions. Regions 17, 25, and 26 lie along a curved line described by the following relationship:

$$\alpha = \cot^{-1}\left[\frac{-1}{2\cot(\beta)}\right]$$

These thresholds are useful to describe the boundaries of each region of FIG. 7. The chart of FIG. 7 also exhibits symmetry about the line α=−β, with corresponding regions on opposite sides of the line having the same translational direction and opposite rotational directions. For example, region 21 has an actuation direction of coordinated CCW/axial contracting screw motion, while region 22 has an actuation direction of coordinated CW/axial contracting screw motion.

Figure 8:
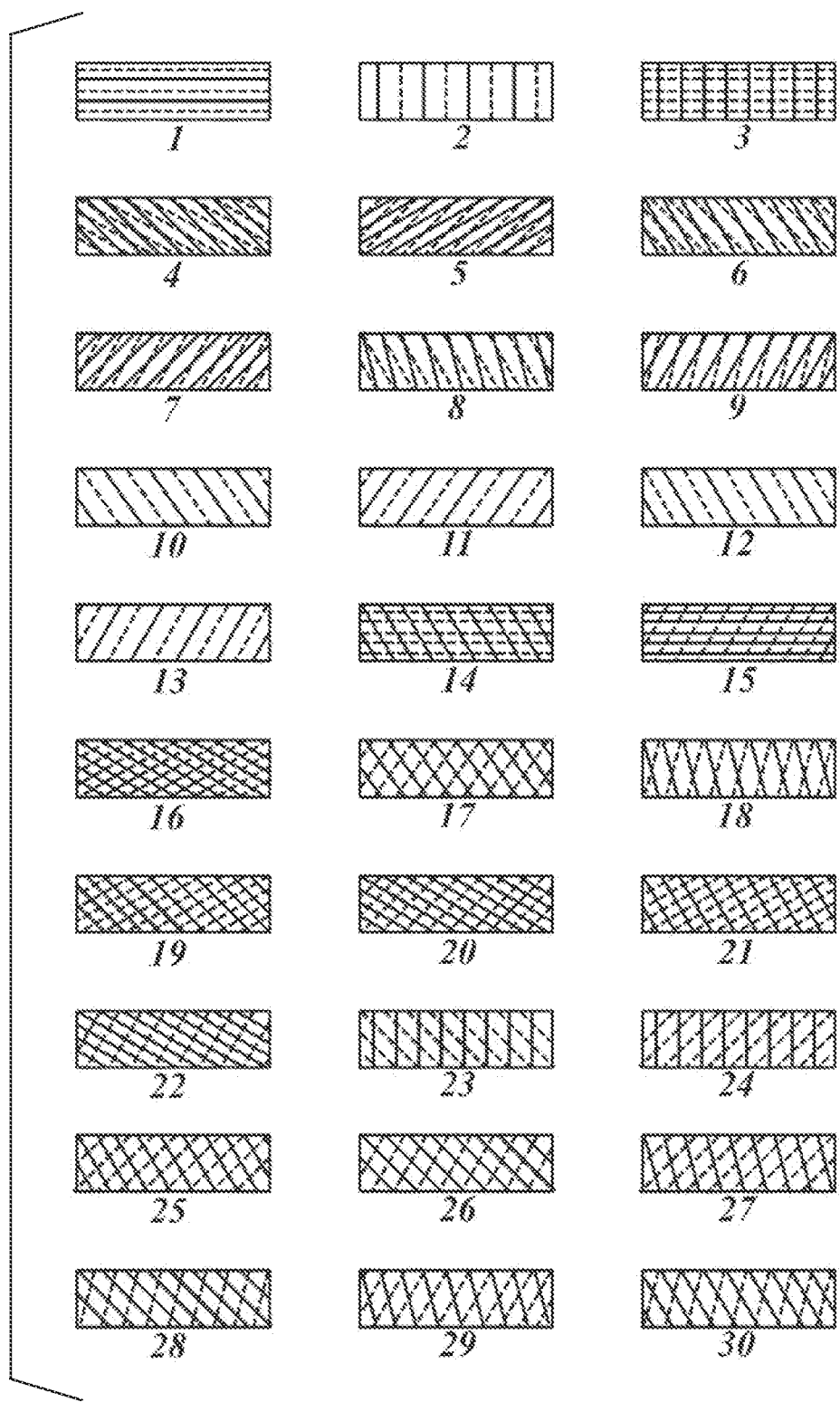
FIG. 8 schematically illustrates regions 1-30 of the chart of FIG. 2 as side views of embodiments of the fiber-reinforced actuator.

FIG. 8 schematically illustrates examples of actuators with fibers configured according to each of regions 1-30. In FIG. 8, the rectangles represent the body of the actuator, the solid lines represent the first set of fibers at angle α, and the broken lines represent the second set of fibers at angle β. The spacing between fibers is schematic, in that straight lines are used in FIG. 8 for simplicity, while fibers extending along cylindrical surfaces would have some apparent curvature and non-uniform spacing when actually viewed from the side.

Fiber configurations that lie along an axis of FIG. 7 (i.e., regions 14 and 15) have purely rotational actuation directions. Fiber configurations that lie along the line α=−β (i.e., regions 16 and 18) have purely translational actuation directions, except region 17. Fiber configurations in accordance with regions 17, 25, and 26 do not have an actuation direction in the sense of providing a force or movement in any direction. These configurations constitute actuators with a locked volume—i.e., the control volume cannot increase when work is performed thereon. Fiber configurations that lie along the line α=β (i.e., regions 1, 2, and 10-13) have the first and second sets of fibers parallel with each other along the actuator body and thus behave as if only one set of fibers is used, effectively negating any affect of the relationship between the angles of different sets of fibers.

TABLE 1 below includes mobility mapping for fiber-reinforced actuators having fiber configurations according to regions 1-30 of FIG. 7. The left column lists the regions as labeled in FIG. 7. Eleven possible mobility directions are given for each region. The letter "A" appears in the table where the mobility direction is an actuation direction, the letter "F" appears in the table where the mobility direction is a freedom direction, and the letters "AF" appear in the table where the mobility direction is a direction that has both actuation and freedom components. An actuation direction is a direction in which the actuator moves, or a direction in which the actuator applies a force if resistance is encountered. A freedom direction is a direction in which the control volume is constant. Locked volumes may be moved in a freedom direction even though they have no actuation direction. A direction with both actuation and freedom components may be considered a secondary actuation direction such that, if the actuator encounters resistance in the primary actuation direction, movement and/or force is exhibited in the AF direction. Anything not listed as an A, F, or AF is a constraint—i.e., a direction that would reduce the control volume or extend the fibers.

TABLE I

| REGION (FIG. 7) | MOBILITY DIRECTION (FIG. 9) | | | | | | | | | | |
| --- | --- | --- | --- | --- | --- | --- | --- | --- | --- | --- | --- |
| | A | B | C | D | E | F | G | H | I | J | K |
| 1 | — | F | F | F | — | — | — | — | — | — | — |
| 2 | A | — | F | F | F | AF | AF | — | — | F | F |
| 3 | — | — | F | F | — | — | — | — | — | — | — |
| 4 | — | A | A | — | F | F | — | A | F | — | AF |
| 5 | — | A | — | A | F | — | F | F | A | AF | — |
| 6 | — | — | AF | — | F | A | — | F | — | — | AF |
| 7 | — | — | — | AF | F | — | A | — | F | AF | — |
| 8 | AF | — | AF | — | F | A | — | F | — | — | AF |
| 9 | AF | — | — | AF | F | — | A | — | F | AF | — |
| 10 | — | — | A | — | F | F | — | F | — | — | AF |
| 11 | — | — | — | A | F | — | F | — | F | AF | — |
| 12 | A | — | A | — | F | A | F | F | — | — | AF |
| 13 | A | — | — | A | F | F | A | — | F | AF | — |
| 14 | — | — | A | — | — | — | — | F | — | — | F |
| 15 | — | — | — | A | — | — | — | — | F | — | — |
| 16 | — | A | — | — | F | — | — | F | F | — | — |
| 17 | F | F | — | — | F | — | — | — | — | — | — |
| 18 | A | — | — | — | F | F | F | — | — | — | — |
| 19 | — | AF | — | — | F | — | — | A | F | — | — |
| 20 | — | AF | — | — | F | — | — | F | A | — | — |
| 21 | — | — | — | — | F | — | — | A | — | — | — |
| 22 | — | — | — | — | F | — | — | — | F | — | — |
| 23 | — | — | F | — | F | A | — | — | — | — | F |
| 24 | — | — | — | F | F | — | A | — | — | F | — |
| 25 | — | — | — | — | F | — | F | A | — | — | — |
| 26 | — | — | — | — | F | F | — | — | F | — | — |
| 27 | — | — | — | — | F | — | A | — | — | — | — |
| 28 | — | — | — | — | F | A | — | — | — | — | — |
| 29 | AF | — | — | — | F | F | A | — | — | — | — |
| 30 | AF | — | — | — | F | A | F | — | — | — | — |

Figure 9:
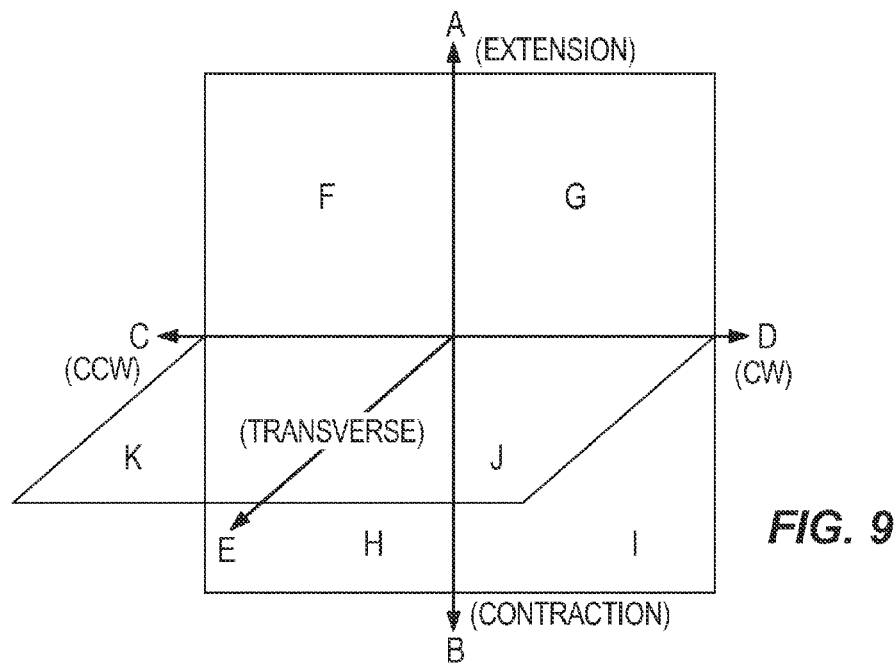
FIG. 9 illustrates the available mobility directions for the fiber-reinforced actuator.

The eleven possible mobility directions are mapped in FIG. 9, where direction A is axial extension, direction B is axial contraction, direction C is counter-clockwise (CCW) rotation, direction D is clockwise (CW) rotation, direction E is transverse bending in all directions, direction F is combined CCW rotation and axial extension, direction G is combined CW rotation and axial extension, direction H is combined CCW rotation and axial contraction, direction I is combined CW rotation and axial contraction, direction J is combined CW rotation and transverse bending, and direction K is combined CCW rotation and transverse bending.

By way of example, a fiber-reinforced actuator with the fibers configured as in region 19 of FIG. 7 has one set of fibers oriented at a positive angle of less than 54.7° and the other set at a negative angle greater than −54.7°, with the magnitude of the positive angle greater than the magnitude of the negative angle. With reference to TABLE I, this configuration has an actuation direction H, freedom directions E and I, and both actuation and freedom components in direction B. Matching these mobility directions with FIG. 9, the actuation directions is coordinated counter-clockwise rotation and axial contraction. Thus, when the control volume of this actuator increases, the actuator will exhibit screw-like motion, twisting and shortening in length. If resistance is encountered against this motion, pure axial contraction may occur. This actuator also has freedom of movement in the combined CW/contraction direction and in the transverse direction.

Fiber-reinforced elastomeric enclosures (FREEs) have been constructed, tested, and characterized to confirm predictable actuation responses described above. Natural latex rubber tubing was used as the actuator body. A rigid or semi-rigid plastic rod or tube may be used as a mandrel to support the flexible wall from the inside of the rubber tubing during construction. Sets of strings or other fibers can then be fixed at one end of the tubing and wrapped in a helical fashion along the outside of the tubing, then fixed at the opposite end of the tubing. One end can be sealed off with a plastic cap. A latex coating (e.g., rubber cement) can then be applied over the string fibers to embed the string in elastomeric material and to fix the location and desired angles of the string. The support rod can be removed from the completed actuator. This is only one simple example of the fiber-reinforced actuator. The number of combinations of materials, shapes, and sizes are virtually limitless.

For example, the body of the actuator in the example of FIG. 6 is a tube with an annular cross-section, where the inner diameter partly defines the control volume. The actuator assumes the general shape of the body when in an unactuated or free state. For a pressure actuated device, the free state is determined either at atmospheric pressure or when the pressure of the control volume is equal to the pressure outside the control volume. Other examples of suitable body shapes include tapered cylinders (i.e., conical or frustoconical shapes), spherical or ellipsoidal shapes, an elongated shape with different diameter cylindrical portions, or an elongated shape with a variable diameter. These examples are all symmetric about a central axis. Non-cylindrical tubes, such as tubes with square or hexagonal cross-sections, may also be employed as the actuator body. In some embodiments, the body is a pre-bent tube or cylinder. A fiber-reinforced actuator with a pre-bent body may be conFigured to straighten when actuated, for example.

The angle of each fiber or each set of fibers need not be constant. The angle of any fiber of a set or of any set of fibers or of a single fiber can change along the length of the actuator body, either as a step change or as a gradual change.

While the above-described FREEs have bodies formed from an elastomeric material, such as natural rubber, the actuator body may be formed from nearly any material. In applications where relatively large movement is desired at low input energy, elastomers or other flexible materials or material combinations may be preferred. Elastomeric materials may also provide a high coefficient of friction in applications where it is intended that force applied to an object by the actuator helps grip the object. Certain fabric or textile materials may also be suitable when low resistance to movement by the body is desired. In some cases, rigid or semi-rigid polymers such as plastics or epoxy materials may be employed as the body material. Metal materials can also be used in the actuator body, such as in applications where high stiffness is required in the free state, where RF shielding or conductivity is required, etc.

In embodiments where the body has a hollow interior, such as with the above-referenced tubular body, the wall thickness may range from a very thin film on the micron scale, to any fraction of the overall width or diameter of the body. Functional FREEs have been constructed with latex tubing having a $\frac{1}{32}$-inch (about 0.030" or 0.8 mm) wall thickness and a $\frac{3}{8}$-inch (0.375" or 9.5 mm) inner diameter. It is also possible to employ a solid body, such as a body material with a high thermal expansion coefficient with which the actuation mechanism is volume change due to temperature change.

The fibers may be any thickness (carbon nanotube or single material chain up to very thick fibers) and may be formed of any of the following materials or any combination of materials. Also, the individual fibers within each of the first and second sets may be formed of the same or different materials or dimensions and, as well, the fibers of one set may be the same or different than the fibers of the other set. The fibers can be natural fibers (e.g., cotton, wool, or bamboo or other bast fibers) or synthetic fibers (e.g., nylon, polyester, Kevlar). Other fiber types include carbon fibers, glass fibers, metal fibers or cables, and hybrid fibers containing a mixture of any of these types of fibers. The fibers may be selected to have high tensile stiffness with negligible stiffness in other directions (i.e., transverse and compressive), such as is the case with thread, string, or rope. The fibers may also take the form of thin beams of metal or plastic that are capable of supporting a compressive axial load. High compressive stiffness fibers or beams may provide actuator deformations that would otherwise buckle fibers. For instance, an actuator configured with cotton string as the fibers with a combination of angular orientations that provide axial contraction when actuated may be made to exhibit transverse bending if one or more of the cotton fibers was replaced with a high-compressive stiffness fiber, such as metal or thick cross-section polymeric fibers. Another type of fiber material is a shape memory alloy, which may be used to add yet another degree of control or functionality to the actuator.

The composition of the control volume can be that of any fluid, such as air, a gas or gas mixture other than air, water, hydraulic fluid, biological fluid (e.g., blood or plasma), magnetic fluid (e.g., rheomagnetic material), or that of any other type of material capable of volume change, such as chemically active materials or combustible materials, which rely on chemical reactions to perform work on the control volume. Electroactive polymers or metals in the control volume may be actuated by application of a voltage. The control volume may also include polymeric materials, such as parylene or foam materials. Fluid absorbing materials may also be employed in the control volume to actuate the device by volume increase due to fluid absorption. The control volume may be composed of or include particles to be used for jamming.

Generally, an increase in volume of the control volume actuates the fiber-reinforced actuator. This volume increase can be accomplished by increased fluid pressure or displacement, increased control volume temperature, decreased pressure outside the control volume, a chemical reaction (e.g., catalyst or combustion reactions), flow restriction into or out of the control volume, or adding additional material to the control volume. As noted above, some actuator configurations have a locked volume and do not accommodate a volume increase. These actuators may still be considered actuated when work is performed on the control volume. For instance, the actuator may exhibit increased stiffness when pressurized or otherwise actuated.

The size of the fiber-reinforced actuator is virtually unlimited as well, ranging from the nanoscale to vary large, such as building or infrastructure size. These actuators may be used alone, coupled together with one or more other fiber-reinforced actuators and/or conventional actuators for more complex motion or high-force generation. The actuators may be employed as springs with the possibility of variable stiffness at two or more different actuation levels or on a continuously variable actuation scale. They may be employed as integrated actuators (including active surfaces), structural members, fluid pumps, shape changing or shape generation devices, end point positioning devices, or volume expanding devices.

Figure 10A:
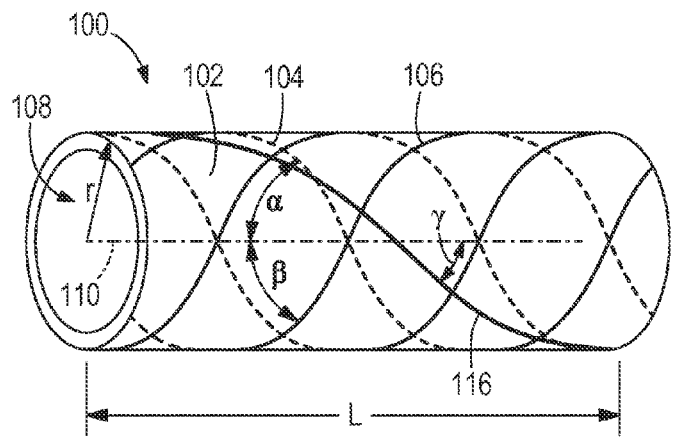
FIG. 10A is a side view of an embodiment of a helical fiber-reinforced actuator in a free state.
Figure 10B:
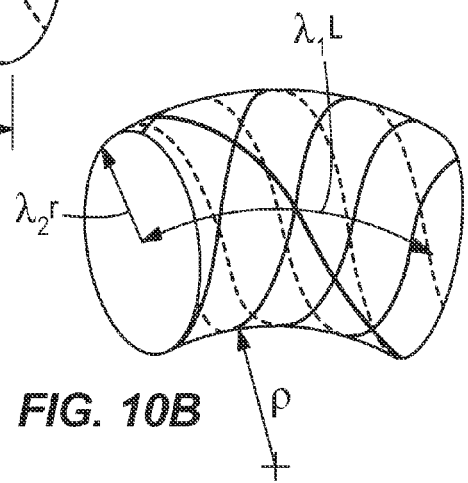
FIG. 10B is a side view of the actuator of FIG. 10A in an actuated state.

Another embodiment of the fiber-reinforced actuator 100 is illustrated in FIG. 10. This example includes an additional single fiber 116 extending along the control volume at a third angle $\gamma$ in addition to the first and second fiber sets 104, 106 described above. This fiber-reinforce actuator may be referred to as a helical actuator, or a helical FREE where the body 102 is elastomeric. FIG. 10A depicts the helical actuator in the free state, and FIG. 10B depicts the helical actuator in an actuated state, illustrating stretching and bending of the portion of the actuator shown in the Figure. In this example, $\gamma \neq 0$ and $\alpha \neq \beta$. In one particular embodiment, $\alpha \neq -\beta$, thus combining the two fiber set configuration of regions 16-18 of FIG. 7 with the additional single fiber 116.

Helical FREEs with latex actuator bodies have been successfully constructed and operated, some examples of which are shown in photographic images in FIGS. 11A-11D. The particular actuator of FIG. 11A has a fiber configuration wherein $\alpha=88°$, $\beta=-60°$, and $\gamma=10°$. The actuator is shown grasping a metal rod and has the ability to support hundreds of times its own weight. The illustrated helical actuator was actuated with a volume increase of 30%. In the actuated state, the helical shape of the actuator had a helix angle of about 56° and a helix radius of about 11.4 mm. FIG. 11B shows the actuator grasping the inner surface of a clear tube. FIG. 11C is another helical actuator configuration with $\alpha=-70°$, $\beta=-30°$, and $\gamma=1°$. The resulting helix angle is about 59° and the resulting helix radius is about 9.3 mm with an actuated volume increase of 35%. FIG. 11D is a photographic image of another helical configuration, with $\alpha=65°$, $\beta=-80°$, and $\gamma=5°$. At an actuated volume increase of 15%, the helix angle is about 9° and the helix radius is about 51°. Each actuator of FIGS. 11A-11D had a body radius of 5.5 mm.

Figure 12:
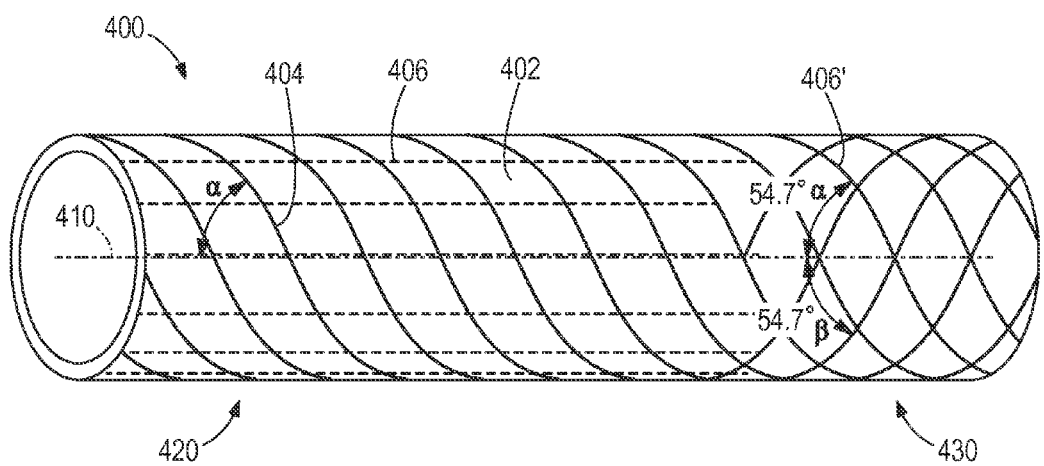
FIG. 12 is a side view of an embodiment of a fiber-reinforced actuator with different fiber configurations along different portions of the actuator body.

FIG. 12 illustrates another embodiment of a fiber-reinforced actuator 400, wherein the fiber configuration is different along first and second portions 420, 430. In this particular example, the first set of fibers 404 are oriented at the same angle $\alpha$ along both of the first and second portions 420, 430 of the body 402, while the second set or sets of fibers are oriented at two different angles $\beta$ at the first and second portions of the body. In FIG. 12, the second set of fibers is labeled as two different second sets, with second set 406 along the first portion 420 of the body and second set 406' along the second portion 430. It is possible, however, that the second sets 406 and 406' are continuous sets for the length of the body 402. At the first portion 420, the first and second sets 404 and 406 are oriented at respective angles of $\alpha=54.7°$ and $\beta=0°$. This corresponds to region 14 of FIGS. 7 and 8. According to TABLE I and FIG. 9, region 14 has only an actuation direction of CCW rotation with no translational component. At the second portion 430, the first and second sets 404 and 406' are oriented at respective angles of $\alpha=54.7°$ and $\beta$-54.7°. This corresponds to region 17 of FIGS. 7 and 8. According to TABLE I and FIG. 9, region 17 has no actuation direction, only freedom directions in translation and transverse bending.

The illustrated actuator 400 is useful as an orthosis device for a person's arm. The first portion 420 can be configured to fit about the user's wrist, and the second portion 430 can be configured to fit along the elbow. In this application, actuation of the orthosis device rotates the wrist and/or forearm of the user. In such an application, it is important that the wrist portion exhibits only rotation, without translation, and is equally important the elbow portion does not actuate with the wrist portion. It is also important that the elbow portion allows for bending. The orientation of the fiber sets can thus be specifically selected for a particular application based on the desired force, moment, degree of freedom, or lack thereof. And different mobility directions can be specified for different portions of the actuator by orienting the fibers in the proper manner.

This is only one of multitudes of potential applications of the fiber-reinforced actuators described and enabled herein. Other types of potential orthotics applications include leg, shoulder, and back orthotics, where the actuators can function as mobility aids, braces with variable stiffness, or powered exoskeletons. Smaller scale orthotics are also possible, such as with fingers and hands. Other potential medical applications include endoscopes, stents, and hospital beds.

Potential aerospace applications include adjustable and/or compliant wings or air foils and complex manipulators. Other potential applications include deployable structures, sensing (e.g., fluid pressure to displacement transducer), grasping (e.g. FREEs as fingers), agricultural robots with soft touch handling of produce, micro-manipulation/assembly, micro flagellum-like motion generation, and active antennas (e.g., changeable shape for frequency tuning).

In these and other applications, actuators can be arranged in parallel concentrically (e.g., one actuator inside another) and/or non-concentrically, arranged in series (e.g., end-to-end), incorporated into meta-material, arranged as sheets of actuators, or arranged with interconnected control volumes, or independent control volumes, or control volumes that selectively interconnect (e.g., via valves). Additional objects or materials may be placed alongside an actuator, such as a thickening element along one side to induce actuator bending motion.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. A crutch comprising:
 a pole;
 a cuff attached to the pole;
 a handle attached to the pole; and
 a forearm support member disposed between the cuff and the handle, the forearm support member having a dimension being changeable, and the forearm support member moveable between a non-constricted position and a constricted position in which the dimension of the forearm support member is increased or reduced respectively;
 wherein: (1) the crutch further comprises an energy generating device to move the forearm support member between the non-constricted position and the constricted position; or (2) the forearm support member comprises a fiber-reinforced actuator.

2. The crutch of claim 1 wherein the crutch comprises a Lofstrand crutch.

3. The crutch of claim 1 wherein the forearm support member comprises an actuator.

4. The crutch of claim 3 wherein the forearm support member comprises the fiber-reinforced actuator.

5. The crutch of claim 4 wherein the forearm support member comprises a fiber-reinforced elastomeric enclosure.

6. The crutch of claim 3 further comprising the energy generating device to move the forearm support member between the constricted position and the non-constricted position.

7. The crutch of claim 6 further comprising an energy storage device to store energy generated by the energy generating device.

8. The crutch of claim 6 wherein the energy generating device is pneumatically-powered or hydraulically-powered.

9. The crutch of claim 6 wherein the energy generating device is electrically-powered.

10. The crutch of claim 6 wherein the energy generating device is mechanically-powered.

11. The crutch of claim 6 wherein the energy generating device is attached to the pole.

12. The crutch of claim 6 further comprising a control member to control when the forearm support member is in the constricted position and when the forearm support member is in the non-constricted position.

13. The crutch of claim 1 further comprising a second forearm support member disposed within the forearm support member.

14. The crutch of claim 13 wherein the second forearm support member comprises at least one shell flexibly attached to the cuff.

15. The crutch of claim 1 further comprising a wrist support member to support a user's wrist in neutral position so that the user's hand and forearm are substantially collinear as the user's hand is gripping the handle.

16. The crutch of claim 15 wherein the wrist support member is attached to the handle or the pole.

17. The crutch of claim 15 wherein the wrist support member is substantially parallel to a portion of the pole.

18. The crutch of claim 15 further comprising a support member to support the user's wrist in the neutral position.

19. A crutch comprising:
   a pole;
   a cuff attached to the pole;
   a handle attached to the pole;
   a forearm support member, comprising an actuator, disposed between the cuff and the handle, the forearm support member having a dimension being changeable, and the forearm support member moveable between a constricted position and a non-constricted position, wherein the dimension of the forearm support member in the constricted position is increased or reduced respectively;
   a second forearm support member disposed within the forearm support member, the second forearm support member having a dimension being changeable; and
   an energy generating device to move the forearm support member between the constricted position and the non-constricted position.

20. The crutch of claim 19 wherein the crutch comprises a Lofstrand crutch.

21. The crutch of claim 19 wherein the forearm support member comprises a fiber-reinforced actuator.

22. The crutch of claim 21 wherein the forearm support member comprises a fiber-reinforced elastomeric enclosure.

23. The crutch of claim 19 wherein the second forearm support member comprises at least one shell flexibly attached to the cuff.

24. The crutch of claim 19 further comprising an energy storage device to store energy generated by the energy generating device.

25. The crutch of claim 19 wherein the energy generating device is pneumatically-powered or hydraulically-powered.

26. The crutch of claim 19 wherein the energy generating device is electrically-powered.

27. The crutch of claim 19 wherein the energy generating device is mechanically-powered.

28. The crutch of claim 19 wherein the energy generating device is attached to the pole.

29. The crutch of claim 19 further comprising a control member to control when the forearm support member is in the constricted position and when the forearm support member is in the non-constricted position.

30. The crutch of claim 19 further comprising a wrist support member to support a user's wrist in neutral position so that the user's hand and forearm are substantially collinear as the user's hand is gripping the handle.

31. The crutch of claim 30 wherein the wrist support member is attached to the handle or the pole.

32. The crutch of claim 30 wherein the wrist support member is substantially parallel to a portion of the pole.

33. The crutch of claim 30 further comprising a support member to support the user's hand in the neutral position.

34. A method of using a crutch comprising:
   inserting a user's hand through a cuff of a crutch and a forearm support member of the crutch, which is disposed between the cuff and a handle of the crutch, wherein the forearm support member is disposed in a non-constricted position;
   gripping the handle of the crutch with the user's hand; and
   moving the forearm support member of the crutch from the non-constricted position to a constricted position in which a dimension of the forearm support member is reduced to engage the user's arm to provide support to the user's forearm;
   wherein: (1) the forearm support member comprises a fiber-reinforced actuator, and moving the forearm support member from the non-constricted position to the constricted position comprises actuating the fiber-reinforced actuator; or (2) moving the forearm support member from the non-constricted position to the constricted position further comprises an energy generating device moving the forearm support member between the constricted position and the non-constricted position.

35. The method of claim 34 wherein the crutch comprises a Lofstrand crutch.

36. The method of claim 34 wherein the forearm support member comprises an actuator, and moving the forearm support member from the non-constricted position to the constricted position comprises actuating the actuator.

37. The method of claim 36 wherein the forearm support member comprises the fiber-reinforced actuator.

38. The method of claim 37 wherein the forearm support member comprises a fiber-reinforced elastomeric enclosure.

39. The method of claim 36 wherein moving the forearm support member from the non-constricted position to the constricted position further comprises the energy generating device moving the actuator between the constricted position and the non-constricted position.

40. The method of claim 39 wherein moving the forearm support member from the non-constricted position to the constricted position further comprises an energy storage device providing stored energy, generated by the energy generating device, to the actuator.

41. The method of claim 39 further comprising powering the energy generating device pneumatically or hydraulically.

42. The method of claim 39 further comprising powering the energy generating device electrically.

43. The method of claim 39 further comprising powering the energy generating device mechanically.

44. The method of claim 39 wherein moving the forearm support member from the non-constricted position to the constricted position further comprises a control member controlling when the forearm support member is in the constricted position and when the forearm support member is in the non-constricted position.

45. The method of claim 34 wherein moving the forearm support member from the non-constricted position to the constricted position further comprises constricting a second forearm support member disposed within the forearm support member to provide support to the user's forearm.

46. The method of claim 45 wherein the second forearm support member comprises at least one shell flexibly attached to the cuff.

47. The method of claim 34 further comprising supporting a user's wrist in a neutral position with a wrist support member of the crutch so that the user's hand and forearm are substantially collinear as the user's hand grips the handle of the crutch.

48. The method of claim 47 wherein the wrist support member is attached to the handle or a pole of the crutch.

49. The method of claim 47 wherein the wrist support member is substantially parallel to a portion of a pole of the crutch.

50. The method of claim 47 further comprising supporting the user's wrist in the neutral position with a support member of the crutch.

\* \* \* \* \*

UNITED STATES PATENT AND TRADEMARK OFFICE
CERTIFICATE OF CORRECTION

PATENT NO. : 9,662,263 B2
APPLICATION NO. : 14/882292
DATED : May 30, 2017
INVENTOR(S) : Elizabeth T. Hsiao-Wecksler et al.

It is certified that error appears in the above-identified patent and that said Letters Patent is hereby corrected as shown below:

On the Title Page

Insert:
--Related U.S. Application Data
(60) Provisional Application No. 62/062,624, filed on Oct. 10, 2014--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*